United States Patent [19]

Stricker

[11] Patent Number: 4,802,650
[45] Date of Patent: Feb. 7, 1989

[54] INTRAVENOUS DRUG MIXING AND FLOW DEVICE

[75] Inventor: Saul Stricker, Marblehead, Mass.

[73] Assignee: Abiomed, Inc., Danvers, Mass.

[21] Appl. No.: 67,940

[22] Filed: Jun. 29, 1987

[51] Int. Cl.⁴ .................. F16K 7/06; F16K 47/08; A61M 5/00
[52] U.S. Cl. .................. 251/117; 251/9; 251/10; 251/7; 604/34; 604/250
[58] Field of Search .................. 251/117, 10, 9, 7; 604/250, 34

[56] References Cited

U.S. PATENT DOCUMENTS

| | | | |
|---|---|---|---|
| 4,267,835 | 5/1981 | Barcer et al. | 251/117 X |
| 4,322,054 | 3/1982 | Campbell | 251/7 X |
| 4,373,524 | 2/1983 | Leibinsohn | 604/250 |
| 4,673,161 | 6/1987 | Flynn et al. | 251/10 |
| 4,718,634 | 1/1988 | Bond | 251/117 |
| 4,743,235 | 5/1988 | Waldbilling et al. | 604/250 |

Primary Examiner—Arnold Rosenthal
Attorney, Agent, or Firm—Lahive & Cockfield

[57] ABSTRACT

A set for the passive infusion of one or more medications at a determined rate includes a fluid supply tube having first and second branched flow paths with first and second rate-defining flow restrictors. An injection port upstream of the first flow restrictor permits injection of a drug to be metered, so the first restrictor provides a metered flow of drug plus carrier, and the second restrictor provides a metered flow of diluent/carrier. A Y-connector, which may contain a mixing element, combines the two flows to provide the desired output flow and drug concentration. Further flow branches, each with an injection port and a flow restrictor, allow additional drugs to be metered in other concentrations. A flushable flow restrictor segment includes a flexible flow tube which may be pinched off, and a substantially rigid capillary tube integral with the flexible tube. End connectors adapt the segment for placement in an infusion line, and a pinch clamp surrounds the flow tube, so that the segment may be opened for flushing yet conveniently clamped to a determined flow rate by the pinch clamp. Various delivery rates are achieved with series or parallel arrangements of such flow restrictor segments. A flow restrictor with a branched end connector connects to a pressure monitor.

7 Claims, 3 Drawing Sheets 4,802,650

INTRAVENOUS DRUG MIXING AND FLOW DEVICE

TECHNICAL FIELD

The present invention relates to devices for the intravenous delivery of drugs and other fluids, and in particular to such devices for the delivery of drugs or fluids at defined rates or defined concentrations.

There are three basic methods used for administering intravenous drugs, with the choice of a particular method determined by the type of drug, the required systemic level, the desired change in level over time and the effect of the drug on the veinous system. The first method is to inject drugs directly into the vein as a bolus. The second method, often referred to as the "IV push" method, consists of injecting up to several cc's of medication into an IV line and allowing a carrier fluid such as saline or dextrose solution to push the medication into the vein over the course of several minutes. This method produces a delay, as well as a slight dilution of the injected drug, thus providing a more gradual introduction of the medication into the veinous system than that achieved by the first, or bolus, method.

Not all drugs are amenable to administration by these two methods however; some must be injected over a much longer period. Some drugs, for instance, must be diluted in order to achieve the required osmolality, or to reduce irritation at the injection site. This class of drugs is generally administered by a third method which uses intermediate containers such as mini-bags, partly filled bottles, or burettes containing the required amount of medication in the correct concentration.

In this third method, the medication is delivered to the IV line via a secondary administration set. Typical of the drugs so administered are Gentamicin, Cephalosporin, Aminophylline, Ranitidine Hydrochloride, Lidocaine, and Isuprel. Some such drugs are unstable in the dilute form at room temperature, hence must be compounded immediately before use, or prepared for storage in frozen form. The use of a secondary fluid supply and the special compounding of the medications in the secondary supplies results in a rather expensive form of drug administration. Various proprietary approaches have been implemented to incorporate a secondary medication source in a primary carrier flow regimen. One such system permits the manufacturer's drug vial to be attached directly to the IV flow line, eliminating the intermediate steps of mixing and storing a solution of the medication.

Ideally, an intravenous medication administering set should minimize the use of high cost disposables, eliminate drug preparation and set up time, and avoid the waste of discarding pre-mixed drug aliquots.

OBJECTS AND SUMMARY OF THE INVENTION

It is an object of the invention to provide an improved intravenous flow device.

It is another object of the invention to provide an intravenous flow device which delivers medication at a controlled dilution rate to a flow line.

It is another object of the invention to provide a passive flow control device having low flow rate yet quick set up time.

According to one aspect of the invention, these and other desirable traits are achieved in an infusion set having a flow restrictor for defining a determined flow rate of infusate wherein the flow restrictor includes a flexible flow tube having first and second ends adapted for fluid connection into the infusion set, and having an interior cross section of the size to not substantially restrict flow through the set. A substantially rigid flow tube integral with the flexible flow tube defines at least in part a parallel flow path between the first and second ends. The rigid flow tube has an interior cross section effective to restrict flow to a determined flow rate. In use, the infusion set is set up by bleeding through the flexible flow tube. A pinch clamp then closes down the flexible tube allowing flow only through the rigid flow tube at the desired low flow rate. Preferably, the rigid flow tube is embedded in the wall of the flexible flow tube. The flexible flow tube may be a fiber reinforced tube, so that it is substantially inextensible and resists pulling or dislocation of the rigid tube contained therein. The rigid flow tube is selected to have a sufficiently thin wall to flex along its axis without collapsing, and to not substantially impair the flexibility of the flexible tube.

According to another aspect of the invention, an infusion set includes a carrier flow member which may, for example, connect to a reservoir of carrier fluid such as saline. The flow member branches downward into first and second arms defining first and second flow paths. An injection port in the first arm allows the introduction of a small bolus of an active liquid, such as a medication, via retrograde injection into the IV line, and a first flow restrictor in the first arm downstream from the injection port determines a flow rate for the active liquid carried by the carrier fluid flowing in the first branch. A second flow restrictor is located in the second arm, and determines a second flow rate for the pure carrier liquid. The outputs of the first and second flow restrictors feed to a common output means which defines the infusion path for connection to a catheter. A first and second flow restrictors may be simple capillary tubes, but preferably are flushable flow restrictors as described above. Preferably the second flow restrictor defines a substantially greater flow rate than the first flow restrictor. In a preferred embodiment, the first flow restrictor includes first and second end connectors for replaceably connecting the flow restrictor between the first arm and the output tube, so that different flow restrictors may be interchanged or interconnected to select a desired flow rate, hence concentration, for a particular medication.

BRIEF DESCRIPTION OF THE DRAWINGS

These and other features of the invention will be understood from the description below of illustrated embodiments, taken together with the figures, wherein.

DETAILED DESCRIPTION OF ILLUSTRATED EMBODIMENTS

Figure 1:
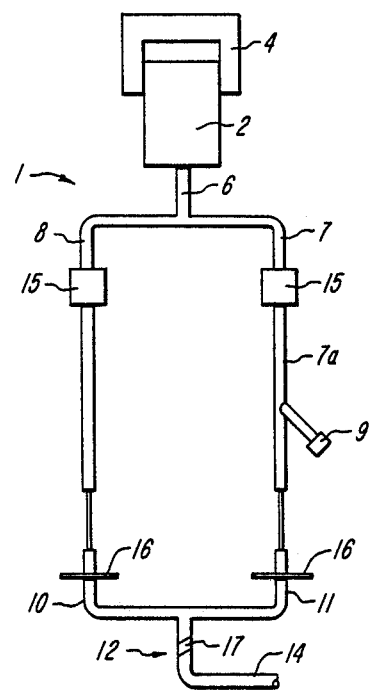
FIG. 1 shows a drug mixing device for administration of medication according to one aspect of the invention.

FIG. 1 shows an intravenous flow device 1 for providing a defined concentration of medication to an intravenous flow line. As shown, an IV bag 2, which may, for example, be a reservoir of saline solution, provides a flow of fluid to a supply conduit 6. Conduit 6 branches into a first branch 7 and a second branch 8. Branch 7 includes an injection port 9 having a polymer plug through which medications may be retrograde injected into the flow line 7. Each branch 7, 8 of the supply conduit has a flow restrictor 11, 10 at its downstream end for determining a specific flow rate through that branch of the set. By flow restrictor is meant a passive flow restriction device, such as a capillary tube, which determines the flow rate, for a fluid of given viscosity, by its cross sectional dimension, length and pressure drop across the restrictor. The lower ends of flow restrictors 11, 10 each connect to a common output manifold 12 which combines the two flow paths into a single output line 14 which may, for example, connect directly to a catheter. The flow in output line 14 has a defined concentration of medication equal to the concentration of medication flowing out of flow restrictor 11, as diluted by the amount of carrier passing through flow restrictor 10.

Thus, the set 1 acts as a mixing device much as an IV administration set with a built in flow restrictor, but with the addition of a side branch having a second flow restrictor and an injection port. This side branch, or the portion thereof labelled 7a, becomes the reservoir for medications introduced by syringe via the injection port by a retrograde "IV push". The drug and the carrier mix together by flowing under the influence of a known driving pressure, supplied in the illustrated embodiment by a pressure cuff 4, through the individual flow restrictors which each determine flow at a defined flow rate. The medication and the diluent in the desired ratio come together at the intersection of the two branches and are delivered to the patient in that ratio, thus avoiding the need for a secondary container or for a separate step of compounding a medication.

In the system of FIG. 1, drip chambers 15, illustrated in schema, are provided on each flow line to permit verification of the flow rate, and slide clamps 16 are placed at the bottom of each branch for cutting off one or more flow lines, as required.

The precise concentration and rate of delivery achieved can be calculated as follows. The flow of liquid through a pipe is governed by Poiseuille's law (1), $$P = 128(\eta L Q)/4\pi d^4 \text{ in CGS units} \quad (1)$$

where
 $\eta$ is the viscosity of the liquid
 L is the length of the tube
 d is the internal diameter of the tube
 P is the driving pressure
 Q is the resulting flow rate.

This formula describes the relationship between flow rate, geometry, pressure, and viscosity. When the values of the variables are determined, it dictates the size of the capillaries required to produce specific flow rates. This formula applies only for laminar flow. However a straightforward calculation shows that normal infusion conditions result in laminar flow.

The Reynolds number is used to determine whether the flow conditions are laminar or turbulent.

$$\text{Reynolds number } dv\rho/\eta \quad (2)$$

where
 v is the fluid velocity
 $\rho$ is the density.

A Reynolds number below 2000 indicates laminar flow, and a number above 3500 represents turbulent flow. Using Equation 1, one can calculate the size of capillaries required to control flow as follows: given a driving pressure of 300 mmHg and desired flow rates of 100 cc/hr for dilutent and 1 cc/hr for the concentrated drug, the required capillaries having a length of 2.5 cm, require diameters of 0.016 and 0.005 cm, respectively, (corresponding to 30 gage and 34 gage capillary tubing). For the 30 gage and 34 gage capillary tubings, the Equation 2 yields respective Reynolds numbers 21 and 69, demonstrating laminar flow under the desired conditions. In this flow regime, the delivery rate of the drug stream and the diluent stream are thus readily controlled and predicted.

Once a bolus of drug is injected into the drug storing branch of the mixing device, and the flow is allowed to begin, the drug will gradually reach the capillary and begin to mix with dilutent flowing down the other branch. As the drug is drawn down, dilutent fills in behind it, until the drug is gone and the delivery is complete. During the draw-down period, a certain amount of mixing between drug and dilutent takes place; this mixing is referred to herein as the primary dilution. As the somewhat dilute drug mixes with the stream of dilutent in the other branch, the main dilution of the drug takes place. This will be called the secondary dilution, and results in precisely the dilution that the patient would receive.

Figure 3:
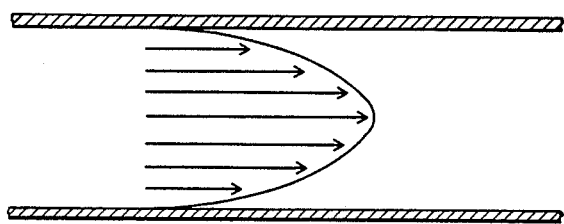
FIGS. 3 to 5 illustrate drug flow in a flow restriction element.
Figure 4:
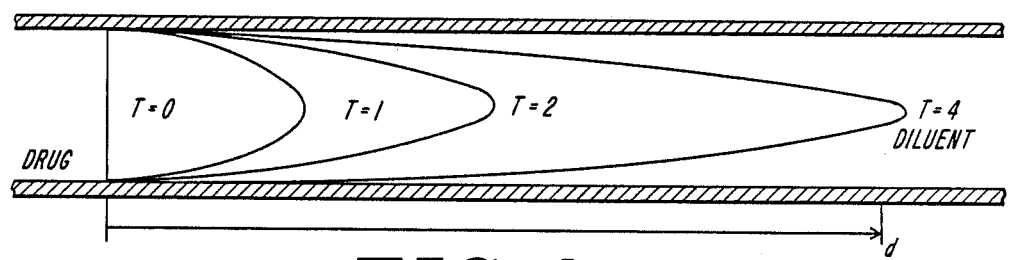
Figure 5:
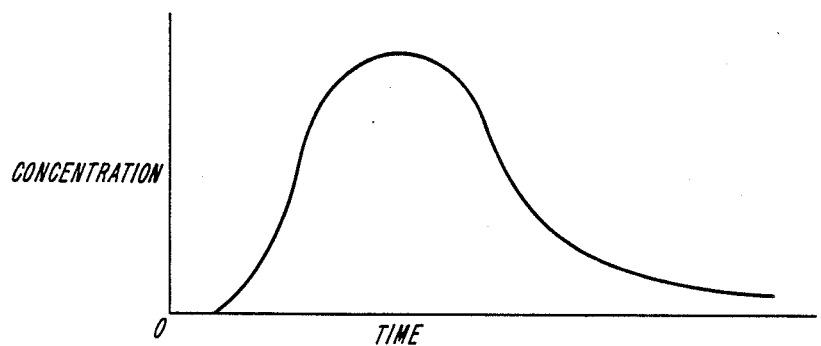

The processes of dilution and mixing in the configuration of the illustrated embodiment of the invention will now be described with reference to FIGS. 3–5.

The Primary Dilution

When a quantity of concentrated drug is introduced at port 9, we may assume that a constant flow is established by a combination of constant driving pressure and the fixed capillary tube 11 downstream. Liquid in the tube will flow fastest at the center of the tube and will be essentially at rest near the wall of the tube due to the viscous drug of the liquid. The velocity profile across a diameter is parabolic, as illustrated in FIG. 3, with the velocity vector at the center equal to twice that of the mean velocity across the section.

Laminar flow may be pictured as a series of concentric cylinders sliding past one another, with no intermixing between cylindrical regions. This flow mechanism dilutes the concentrated drug by controlled transport of diluent and drug to a collection point, where it is mixed. Mixing does not take place in transit during laminar flow, unless other mechanisms are acting, as discussed later.

As the liquid moves downstream, the cylinders near the center travel much further than those near the wall due to their higher velocity. FIG. 4 illustrates a sequence of positions of the original interface of dilutent and drug in a flow tube at four different times.

At the latest time illustrated, T=4, the central, faster moving cylinders of liquid have transported drug a distance d=velocity x time. A sample of the constitution of a thin cross-section of liquid at that distance d would show a small amount of drug in dilutent. As time goes on, the amount of drug in the composition crossing station d increases as the slower moving cylinders arrive at d. As the volume of drug upstream becomes depleted, the concentration starts declining and approaches zero.

In summary, the delivery pattern of this configuration will have a small delay, a peak concentration, and an exponential decline. This concentration curve is illustrated in FIG. 5. That is, FIG. 5 shows the form of the primary dilution which occurs in the medication branch of flow device 1.

The Secondary Dilution

After primary dilution, the partly diluted solution of drug and diluent emerging from the branch containing the drug will be brought together with the second branch which preferably carries a much faster flowing stream of diluent, to obtain the required final level of dilution. The concentration of drug after secondary dilution has a shape over time similar to that of FIG. 5, but at a correspondingly lower concentration, reduced proportionate to the carrier flow in the second branch.

As the two streams come together, the drug concentration is reduced due to the added diluent from the second branch. However, due to laminar flow in the line it is possible that little or no mixing of the streams may take place. Preferably also the flow device 1 includes an element to mix the two streams prior to infusing the fluid. This may be accomplished with a passive element such as a matrix filter, shown as 17 in FIG. 1. It is expected that in practice the provision of a mixing element will not be necessary, since the stream will have a consistent composition of drug and diluent over time due to the spreading inherent in laminar flow. Thus, such local variations as may exist across the flow tube section at a given time should not impair the overall uniformity of delivery.

It will be further appreciated that a drug mixing system according to the invention may include more than one primary drug mixing line 7, and that with due attention to the compatibility of drugs, additional drugs may be diluted by passing through flow restrictors in additional branches and joining with one or more branches carrying the diluent or another drug to a common outlet 14 which combines the plural drugs and carrier in a defined ratio as a single outflow. Thus, plural parallel pairs of branches like 7, 8 of FIG. 1 may connect to a common outlet manifold, or plural branches with injection ports like branch 7 may connect to a single diluent-carrying branch 8, to provide such multi-drug metering.

The flow restrictors 10, 11 may be capillary tubes having lengths and diameters calculated according to equation 1 to provide the desired total flow rate and drug concentration. According to another aspect of applicant's invention, however, each flow restrictor has a special construction for convenient flushing of the flow line.

Figure 2A:
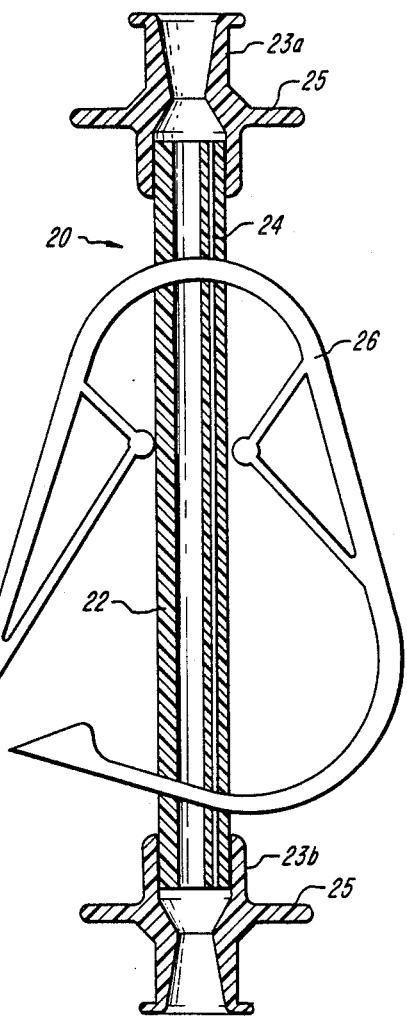
FIGS. 2A and 2B show flushable flow restriction elements according to another aspect of the invention.
Figure 2B:
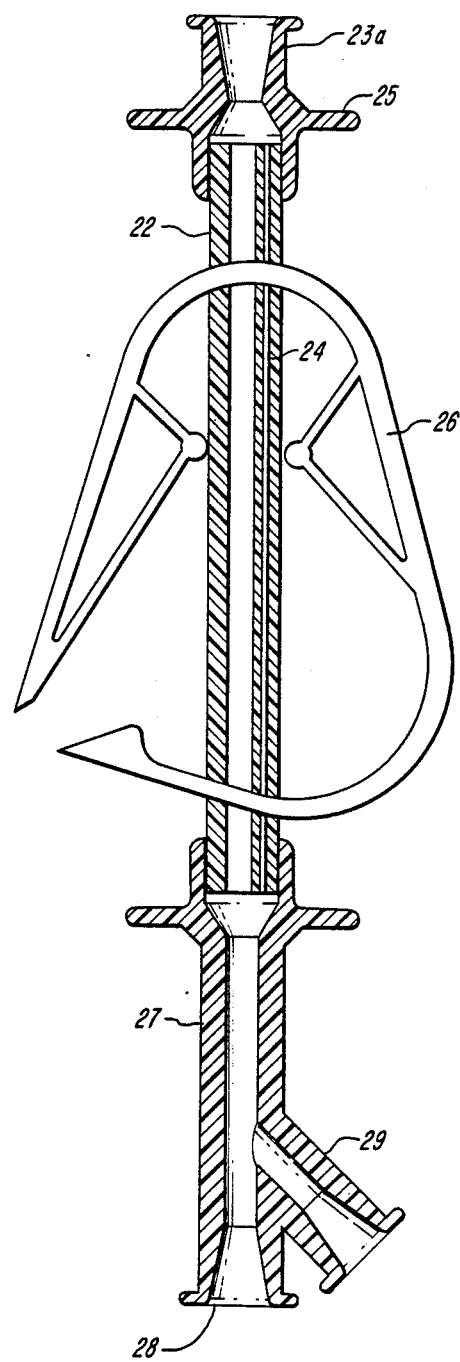

According to this aspect of the invention, a flow restrictor includes a flexible flow tube having an interior cross section of a size to not substantially restrict flow through the infusion set, and a substantially rigid restriction tube integral with the flexible flow tube and defining at least in part a parallel but restricted flow path. A pinch clamp is placed about both the flexible and rigid tube. In the open state, flushing of the flow segment is accomplished through the flexible tube. When closed, the pinched clamp entirely cuts off flow through the flexible tube but does not affect the rigid capillary tube, so that flow is restricted to the level defined by that rigid tube. Thus, by "rigid" is meant that the capillary tube is sufficiently stiff that its cross-section is unaffected by the pinch clamp. FIGS. 2A and 2B show different embodiments of a flow control device according to this aspect of the invention for incorporation in an infusion set.

As shown in FIG. 2A, a flow restriction segment includes a flexible tube 22 having a capillary tube 24 embedded in a wall thereof. Standard IV tubing connectors 23a, 23b adapt the ends of the flow segment for connection to conventional IV tubing. A pinch clamp 26 is fitted about the tube and may, for example, be constrained thereon by flanges 25 of the connectors.

The construction of a flow restrictor as just described addresses the problem of flushing air from a pressurized source of liquid through a flow line having a restrictor for regulating the rate of delivery. In setting up an infusion set, all air must be flushed from the line quickly and effectively. Since the flow restrictor conventionally determines the rate of fluid flow through an infusion line, is generally necessary to bypass the restriction by removing it or temporarily opening a second flow line. By way of example, if a flow restrictor has a delivery rate of 50 cc/hr and is installed in an administration set having a volume of 15 cc, it would take as long as 18 minutes to flush trapped air bubbles from the infusion set through the flow restrictor.

According to a further aspect of the invention, several flow restriction segments may be connected in series or in parallel for a variety of applications. For example, connecting three of the devices in series with flow rates of 20, 40, and 60 cc/hr, respectively, allows the selection of the 20, 40, or 60 cc/hr flow rate by pinching the appropriate clamp closed and leaving the other two open. Lesser flow rates may be obtained by closing two pinch valves of the series. By connecting three devices in parallel flow lines, different fluids in each line may be administered at different rates, or as described above with reference to FIG. 1, an active liquid and a carrier liquid may be passively diluted and mixed together to administer medications at a controlled rate.

The construction illustrated in FIG. 2A replaces prior art constructions and allows convenient incorporation into rate selection or mixing systems. It has no extraneous branches, and is of simple construction. The catheter flushing and flow control device consist of three components: a body consisting of a length of flexible tubing, a length of rigid capillary tubing embedded in the wall of the flexible tubing, and an external pinch clamp. Luer lock connectors at each end of the tubing permit connection of the device to ordinary IV pressure monitoring tubing. When the pinch clamp is open, the lumen of the flexible tube is wide open and the line can be flushed. When the pinch clamp is closed, the flow through the lumen of the flexible tube stops completely. The flow through the capillary tube continues unchanged at a rate which depends essentially upon the pressure difference across the tube, the length of the capillary, its diameter, and the viscosity of the liquid.

The rate of flow, Q, may be derived from equation (1) above as $$Q = (\pi d^4 \Delta P)/(128 \eta L) \tag{3}$$

where Q is the laminar flow rate, d is the tube diameter, $\Delta P$ is the pressure difference across the tube, $\eta$ is the viscosity of the liquid, and L is the length of the tube.

The connectors may be Luer fittings or solvent bonded sleeve fittings, depending on the intended application.

FIG. 2B shows another embodiment of a flow restrictor according to the invention, adapted for arterial pressure monitoring. This application requires that a constant low flow of saline be maintained in an arterial catheter used to monitor pressure in order to prevent clotting off of the pathway. Usual rates of flow for this "keep open" saline infusion are around 2 cc/hr. To flush a 10 cc infusion set through such a flow restrictor could take five hours. Devices exist which permit bypassing the flow restrictor by squeezing or pulling a portion of the device to activate a temporary bypass. The bypass is normally closed and is operated to flush air out of the line before use and to periodically clear the catheter of any partial blockage.

As shown in FIG. 2B, the flushable flow restrictor of FIG. 2A is readily adapted as a keep open flow device. Corresponding parts of the embodiment in FIG. 2B are labeled identically to those of FIG. 2A. The lower sleeve 23b of the device illustrated in FIG. 2A, however, is replaced in the device of FIG. 2B by a fitting 27 in the form of a Y-connector having branched outlet lines. A first outlet 28 connects to an arterial pressure catheter, and a second outlet 29 in direct pressure communication therewith adapts the device for connection to a pressure transducer for monitoring arterial pressure. Outlet 23a connects the device to a pressurized source of liquid for providing a continuous flush. During normal operation of such a device, the clamp 26 would be in the closed position. A fast flush is accomplished by momentarily opening the clamp and then reclosing it.

According to a preferred embodiment of a flushable flow restrictor according to the invention, the flexible tubing 22 has a wall fabricated with a fiber reinforcing strands made of non-stretch material such as polyester, nylon, or the like in order to render the tube wall unstretchable and to prevent dislocation and detachment of the rigid capillary embedded therein. This prevents bypass leakage via the space between the capillary and tubing walls, and further prevents the possible oclusion of a capillary end which might otherwise occur if the capillary were to recede longitudinally within the flexible tube wall and become blocked by material thereof.

It is contemplated that flushable flow restriction segments according to this aspect of the invention may be fabricated by insert molding in a process wherein a length of steel capillary tubing is placed within an injection mold and the flexible tubing is then formed in the mold about the capillary tube. Another manufacturing method is to extrude the plastic tubing either with a separate lumen for receiving the capillary tube, or extruding it with the capillary tube plus fiber reinforcing strands in a single process. This latter approach lends itself to high volume production rates. A suitable cutting tool for cutting segments of the tubing without closing off the lumen of the capillary is then used to provide flow segments of the desired lengths, after which the end connectors are fitted and bonded thereto.

It will be appreciated that the invention has been described with reference to the illustrated embodiments for convenience of understanding, and that this description is intended as illustrative of the invention, and not in limitation thereof. The invention being thus disclosed, other variations and modifications will occur to those of ordinary skill in the art, and such variations and modifications are believed to be within the scope of the invention as defined by the following claims.

What is claimed is:

1. A flow restrictor for inclusion in an infusion flow path to define a determined flow rate of infusate, such flow restrictor comprising a first flow tube having a peripheral wall and first and second ends with first and second end connectors adapted for fluid connection into an infusion set, said peripheral wall defining a continuous normally open passage with an interior cross section of a size to not substantially restrict flow through said set, said peripheral wall further being flexible such that opposed regions thereof may be pinched together to occlude the normally open passage, and a second flow tube integral with said peripheral wall and defining at least in part a parallel flow path between said first and second ends, said second flow tube being adapted to restrict flow to said determmmined flow rate, and being substantially rigid so that the parallel flow path remains open when said peripheral wall is clamped thereby assuring that fluid flows at at least said determined rate.

2. A flow restrictor according to claim 1, wherein said second flow tube is a capillary tube at least partially embedded within the peripheral wall of said first flow tube.

3. A flow restrictor according to claim 1, further comprising a pinch clamp fitted about said flow restrictor and retained thereon by said end connectors.

4. A flow restrictor according to claim 2, further comprising a pinch clamp.

5. A flow restrictor according to claim 2, wherein said peripheral wall is substantially inextensible.

6. A flow restrictor according to claim 5, wherein said peripheral wall is fiber reinforced.

7. A flow restrictor according to claim i, wherein a said end connector is a branches end connector adapted for connection with a pressure monitor.

* * * * *